(12) United States Patent
Besaw et al.

(10) Patent No.: US 11,918,489 B2
(45) Date of Patent: Mar. 5, 2024

(54) EXPANSION DRIVER

(71) Applicant: NuVasive, Inc., San Diego, CA (US)

(72) Inventors: Christopher Besaw, San Diego, CA (US); Thomas Sweeney, III, San Diego, CA (US); Christopher Stein, San Diego, CA (US)

(73) Assignee: Nuvasive Inc., San Diego, CA (US)

( * ) Notice: Subject to any disclaimer, the term of this patent is extended or adjusted under 35 U.S.C. 154(b) by 0 days.

(21) Appl. No.: 18/006,411

(22) PCT Filed: Mar. 31, 2022

(86) PCT No.: PCT/US2022/022807
§ 371 (c)(1),
(2) Date: Jan. 23, 2023

(87) PCT Pub. No.: WO2022/212694
PCT Pub. Date: Oct. 6, 2022

(65) Prior Publication Data
US 2024/0009000 A1    Jan. 11, 2024

Related U.S. Application Data

(60) Provisional application No. 63/170,345, filed on Apr. 2, 2021.

(51) Int. Cl.
*A61F 2/46* (2006.01)
*A61F 2/44* (2006.01)
*A61F 2/30* (2006.01)

(52) U.S. Cl.
CPC .......... *A61F 2/4611* (2013.01); *A61F 2/4455* (2013.01); *A61F 2002/30579* (2013.01); *A61F 2002/4627* (2013.01)

(58) Field of Classification Search
CPC ...... A61F 2/4611; A61F 2/442; A61F 2/4455; A61F 2002/30523; A61F 2002/30579; A61F 2002/4627; F16H 1/222
(Continued)

(56) References Cited

U.S. PATENT DOCUMENTS

| 5,554,191 A | 9/1996 | Lahille et al. | |
| 5,647,254 A * | 7/1997 | Cook, Jr. | B25B 23/145 |
| | | | 81/475 |

(Continued)

FOREIGN PATENT DOCUMENTS

| CN | 100584283 C | 1/2010 |
| EP | 2226039 A1 | 9/2010 |

(Continued)

OTHER PUBLICATIONS

International Search Report and Written Opinion, PCT/US2022/022807, pp. 1-11 (dated Aug. 5, 2022).

*Primary Examiner* — Jessica Weiss

(57) ABSTRACT

This disclosure includes an expansion driver for adjusting expandable implants, the expansion driver including an input shaft operably connected to at least one bevel gear, the at least one bevel gear configured to engage each of a first gear and a second gear; the first gear connected to a first output shaft, the first output shaft terminating in a first driver configured to communicate with a first actuator of an expandable implant; the second gear connected to a second output shaft, the second output shaft annularly disposed around at least a portion of the first output shaft; and at least one pinion configured to transfer a torque from the second output shaft to a second driver extending parallel to the first driver and configured to communicate with a second actuator of the expandable implant. Upon a rotation of the input shaft, a torque is applied to at least one of the first driver and the second driver.

18 Claims, 8 Drawing Sheets

(58) Field of Classification Search
USPC .................. 623/17.11–17.16; 606/99–100
See application file for complete search history.

(56) References Cited

U.S. PATENT DOCUMENTS

| | | | |
|---|---|---|---|
| 5,865,848 A | 2/1999 | Baker | |
| 6,045,579 A | 4/2000 | Hochshuler et al. | |
| 6,126,665 A * | 10/2000 | Yoon | A61B 17/062 |
| | | | 606/144 |
| 6,136,031 A | 10/2000 | Middleton | |
| 6,176,882 B1 | 1/2001 | Biedermann et al. | |
| 6,395,035 B2 | 5/2002 | Bresina et al. | |
| 6,436,142 B1 | 8/2002 | Paes et al. | |
| 6,443,990 B1 | 9/2002 | Aebi et al. | |
| 6,451,057 B1 | 9/2002 | Chen et al. | |
| 6,719,796 B2 | 4/2004 | Cohen et al. | |
| 6,821,298 B1 | 11/2004 | Jackson | |
| 7,128,760 B2 | 10/2006 | Michelson | |
| 7,217,291 B2 | 5/2007 | Zucherman et al. | |
| 7,763,028 B2 | 7/2010 | Lim et al. | |
| 7,819,921 B2 | 10/2010 | Grotz | |
| 7,837,734 B2 | 11/2010 | Zucherman et al. | |
| 7,985,256 B2 | 7/2011 | Grotz et al. | |
| 8,105,382 B2 | 1/2012 | Olmos et al. | |
| 8,398,713 B2 | 3/2013 | Weiman | |
| 8,435,298 B2 | 5/2013 | Weiman | |
| 8,454,617 B2 | 6/2013 | Schaller et al. | |
| 8,465,547 B2 | 6/2013 | Melkent et al. | |
| 8,491,659 B2 | 7/2013 | Weiman | |
| 8,496,706 B2 | 7/2013 | Ragab et al. | |
| 8,568,481 B2 | 10/2013 | Olmos et al. | |
| 8,628,578 B2 | 1/2014 | Miller et al. | |
| 8,632,595 B2 | 1/2014 | Weiman | |
| 8,679,161 B2 | 3/2014 | Malandain et al. | |
| 8,795,366 B2 | 8/2014 | Varela | |
| 8,845,731 B2 | 9/2014 | Weiman | |
| 8,845,732 B2 | 9/2014 | Weiman | |
| 8,845,734 B2 | 9/2014 | Weiman | |
| 8,894,711 B2 | 11/2014 | Varela | |
| 8,894,712 B2 | 11/2014 | Varela | |
| 8,940,049 B1 | 1/2015 | Jimenez et al. | |
| 9,039,771 B2 | 5/2015 | Glerum et al. | |
| 9,125,757 B2 | 9/2015 | Weiman | |
| 9,220,610 B2 | 12/2015 | Chen | |
| 9,233,007 B2 | 1/2016 | Sungarian et al. | |
| 9,314,348 B2 | 4/2016 | Emstad | |
| 9,320,610 B2 | 4/2016 | Alheidt et al. | |
| 9,358,129 B2 | 6/2016 | Weiman | |
| 9,364,339 B2 | 6/2016 | Mayer | |
| 9,370,434 B2 | 6/2016 | Weiman | |
| 9,402,739 B2 | 8/2016 | Weiman et al. | |
| 9,445,919 B2 | 9/2016 | Palmatier et al. | |
| 9,486,328 B2 | 11/2016 | Jimenez et al. | |
| 9,492,288 B2 | 11/2016 | Wagner et al. | |
| 9,522,070 B2 | 12/2016 | Flower et al. | |
| 9,561,116 B2 | 2/2017 | Weiman et al. | |
| 9,585,766 B2 | 3/2017 | Robinson | |
| 9,585,767 B2 | 3/2017 | Robinson | |
| 9,622,878 B2 | 4/2017 | Grotz | |
| 9,662,224 B2 | 5/2017 | Weiman et al. | |
| 9,668,876 B2 | 6/2017 | Blain et al. | |
| 9,668,879 B2 | 6/2017 | Jimenez et al. | |
| 9,713,536 B2 | 7/2017 | Foley et al. | |
| 9,717,601 B2 | 8/2017 | Miller | |
| 9,750,618 B1 | 9/2017 | Daffinson et al. | |
| 9,795,493 B1 | 10/2017 | Bannigan | |
| 9,801,733 B2 | 10/2017 | Wolters et al. | |
| 9,801,734 B1 | 10/2017 | Stein et al. | |
| 9,839,528 B2 | 12/2017 | Weiman et al. | |
| 9,855,151 B2 | 1/2018 | Weiman | |
| 9,861,494 B2 | 1/2018 | Grotz | |
| 9,872,778 B2 | 1/2018 | Grotz | |
| 9,931,226 B2 | 4/2018 | Kurtaliaj et al. | |
| 9,956,087 B2 | 5/2018 | Seifert et al. | |
| 9,962,270 B2 | 5/2018 | Alheidt et al. | |
| 9,987,144 B2 | 6/2018 | Seifert et al. | |
| 9,999,515 B1 | 6/2018 | Grotz | |
| 10,022,239 B1 | 7/2018 | Lentner et al. | |
| 10,034,765 B2 | 7/2018 | Blain et al. | |
| 10,034,769 B2 | 7/2018 | Baynham | |
| 10,039,650 B2 | 8/2018 | Lamborne et al. | |
| 10,052,214 B2 | 8/2018 | Jimenez et al. | |
| 10,076,423 B2 | 9/2018 | Miller et al. | |
| 10,085,846 B2 | 10/2018 | Grotz | |
| 10,098,757 B2 | 10/2018 | Logan et al. | |
| 10,111,758 B2 | 10/2018 | Robinson | |
| 10,154,911 B2 | 12/2018 | Predick et al. | |
| 10,154,914 B2 | 12/2018 | Robinson | |
| 10,172,718 B2 | 1/2019 | Wolters et al. | |
| 10,195,050 B2 | 2/2019 | Palmatier et al. | |
| 10,226,356 B2 | 3/2019 | Grotz | |
| 10,238,503 B2 | 3/2019 | Branch et al. | |
| 10,278,830 B1 | 5/2019 | Walker et al. | |
| 10,278,831 B2 | 5/2019 | Sandul | |
| 10,285,819 B2 | 5/2019 | Greenhalgh | |
| 10,285,820 B2 | 5/2019 | Greenhalgh | |
| 10,285,824 B2 | 5/2019 | Robinson | |
| 10,292,828 B2 | 5/2019 | Greenhalgh | |
| 10,292,830 B2 | 5/2019 | McLuen et al. | |
| 10,299,934 B2 | 5/2019 | Seifert et al. | |
| 10,314,719 B2 | 6/2019 | Hessler et al. | |
| 10,322,011 B2 | 6/2019 | Baynham | |
| 10,327,917 B2 | 6/2019 | Glerum et al. | |
| 10,350,081 B2 | 7/2019 | Seifert et al. | |
| 10,350,084 B1 | 7/2019 | Lin et al. | |
| 10,350,085 B2 | 7/2019 | Glerum et al. | |
| 10,363,142 B2 | 7/2019 | McClintock et al. | |
| 10,369,004 B2 | 8/2019 | Faulhaber | |
| 10,369,010 B2 | 8/2019 | Robinson et al. | |
| 10,376,377 B2 | 8/2019 | Seifert et al. | |
| 10,383,741 B2 | 8/2019 | Butler et al. | |
| 10,390,960 B2 | 8/2019 | Bannigan et al. | |
| 10,390,962 B2 | 8/2019 | Weiman | |
| 10,390,963 B2 | 8/2019 | Olmos et al. | |
| 10,398,563 B2 | 9/2019 | Engstrom | |
| 10,398,566 B2 | 9/2019 | Olmos et al. | |
| 10,398,567 B2 | 9/2019 | Robinson | |
| 10,413,421 B2 | 9/2019 | Arnold et al. | |
| 10,413,422 B2 | 9/2019 | Flower et al. | |
| 10,420,654 B2 | 9/2019 | Logan et al. | |
| 10,426,632 B2 | 10/2019 | Butler et al. | |
| 10,441,430 B2 | 10/2019 | Ludwig et al. | |
| 10,449,056 B2 | 10/2019 | Cain | |
| 10,492,924 B2 | 12/2019 | Stein et al. | |
| 10,500,064 B2 | 12/2019 | Robinson | |
| 10,507,116 B2 | 12/2019 | Shoshtaev | |
| 10,512,550 B2 | 12/2019 | Bechtel et al. | |
| 10,524,924 B2 | 1/2020 | Davenport et al. | |
| 10,531,964 B2 | 1/2020 | Miller et al. | |
| 10,575,964 B2 | 3/2020 | Robinson | |
| 10,575,966 B2 | 3/2020 | Logan et al. | |
| 10,583,015 B2 | 3/2020 | Olmos et al. | |
| 10,610,376 B2 | 4/2020 | Kuyler et al. | |
| 10,610,377 B2 | 4/2020 | Baynham | |
| 10,617,533 B2 | 4/2020 | Glerum et al. | |
| 10,624,761 B2 | 4/2020 | Davenport et al. | |
| 10,631,998 B2 | 4/2020 | Wu et al. | |
| 10,639,166 B2 | 5/2020 | Weiman et al. | |
| 10,646,351 B2 | 5/2020 | Blain et al. | |
| 10,667,927 B2 | 6/2020 | Lamborne et al. | |
| 10,682,239 B2 | 6/2020 | Hsu et al. | |
| 10,682,241 B2 | 6/2020 | Glerum et al. | |
| 10,687,963 B2 | 6/2020 | Jimenez et al. | |
| 10,973,650 B2 | 4/2021 | Stein | |
| 11,234,833 B2 | 2/2022 | Brotman et al. | |
| 11,273,047 B2 | 3/2022 | Besaw et al. | |
| 11,298,243 B2 * | 4/2022 | Himmelberger | A61F 2/4611 |
| 11,554,025 B1 * | 1/2023 | Sweeney, III | A61F 2/4611 |
| 2002/0045945 A1 | 4/2002 | Liu et al. | |
| 2004/0087947 A1 | 5/2004 | Lim et al. | |
| 2006/0155297 A1 * | 7/2006 | Ainsworth | A61F 2/4425 |
| | | | 606/99 |
| 2006/0247781 A1 | 11/2006 | Francis et al. | |
| 2009/0222100 A1 | 9/2009 | Cipoletti et al. | |

(56) References Cited

U.S. PATENT DOCUMENTS

| | | |
|---|---|---|
| 2009/0292361 A1 | 11/2009 | Lopez |
| 2010/0016971 A1* | 1/2010 | Berry .................. A61F 2/44 623/17.15 |
| 2010/0145455 A1 | 6/2010 | Simpson et al. |
| 2010/0160984 A1* | 6/2010 | Berry .................. A61F 2/4611 606/86 A |
| 2011/0015742 A1 | 1/2011 | Hong |
| 2011/0112644 A1 | 5/2011 | Zilberstein et al. |
| 2011/0160861 A1 | 6/2011 | Jimenez et al. |
| 2013/0231747 A1 | 9/2013 | Olmos et al. |
| 2014/0236296 A1 | 8/2014 | Wagner et al. |
| 2014/0236297 A1 | 8/2014 | Iott et al. |
| 2014/0288652 A1 | 9/2014 | Boehm et al. |
| 2015/0066145 A1* | 3/2015 | Rogers .................. A61F 2/4611 623/17.15 |
| 2015/0101432 A1* | 4/2015 | Gao .................. B25B 17/02 74/405 |
| 2015/0272743 A1 | 10/2015 | Jimenez et al. |
| 2015/0374508 A1 | 12/2015 | Sandul |
| 2016/0022434 A1 | 1/2016 | Robinson |
| 2016/0166396 A1 | 6/2016 | McClintock |
| 2016/0167205 A1* | 6/2016 | Wang .................. B25B 15/04 81/58.3 |
| 2016/0256291 A1 | 9/2016 | Miller |
| 2017/0105844 A1 | 4/2017 | Kuyler et al. |
| 2017/0112630 A1 | 4/2017 | Kuyler et al. |
| 2017/0119542 A1 | 5/2017 | Logan et al. |
| 2017/0135824 A1 | 5/2017 | Suddaby et al. |
| 2017/0143507 A1 | 5/2017 | Flower et al. |
| 2017/0151065 A1 | 6/2017 | Warren et al. |
| 2017/0216049 A1 | 8/2017 | Grotz |
| 2017/0224504 A1 | 8/2017 | Butler et al. |
| 2017/0224505 A1 | 8/2017 | Butler et al. |
| 2017/0231780 A1 | 8/2017 | D'Urso |
| 2017/0281358 A1 | 10/2017 | Wagner et al. |
| 2017/0290674 A1 | 10/2017 | Olmos et al. |
| 2017/0290675 A1 | 10/2017 | Olmos et al. |
| 2017/0290676 A1 | 10/2017 | Olmos et al. |
| 2017/0290677 A1 | 10/2017 | Olmos et al. |
| 2017/0290678 A1 | 10/2017 | Olmos et al. |
| 2017/0333198 A1 | 11/2017 | Robinson |
| 2018/0036138 A1 | 2/2018 | Robinson |
| 2018/0064551 A1 | 3/2018 | Stein et al. |
| 2018/0125677 A1* | 5/2018 | Burrows-Ownbey ................... A61F 2/447 |
| 2018/0147065 A1 | 5/2018 | Daffinson et al. |
| 2018/0147066 A1 | 5/2018 | Daffinson et al. |
| 2018/0161171 A1 | 6/2018 | Frasier et al. |
| 2018/0161175 A1 | 6/2018 | Frasier et al. |
| 2018/0193160 A1 | 7/2018 | Hsu et al. |
| 2018/0296361 A1 | 10/2018 | Butler et al. |
| 2018/0303625 A1 | 10/2018 | Alheidt et al. |
| 2018/0333273 A1 | 11/2018 | Blain et al. |
| 2018/0360615 A1 | 12/2018 | Miller et al. |
| 2019/0008649 A1 | 1/2019 | Logan et al. |
| 2019/0008657 A1 | 1/2019 | Amborne et al. |
| 2019/0021868 A1 | 1/2019 | Ludwig et al. |
| 2019/0021870 A1 | 1/2019 | Jimenez et al. |
| 2019/0021872 A1 | 1/2019 | Robinson |
| 2019/0038283 A1* | 2/2019 | Shelton, IV .......... A61B 34/30 |
| 2019/0133780 A1 | 5/2019 | Matthews et al. |
| 2019/0133788 A1 | 5/2019 | Weiman et al. |
| 2019/0142602 A1 | 5/2019 | Olmos et al. |
| 2019/0151110 A1 | 5/2019 | Faulhaber |
| 2019/0201209 A1 | 7/2019 | Branch et al. |
| 2019/0231552 A1 | 8/2019 | Sandul |
| 2019/0240039 A1 | 8/2019 | Walker et al. |
| 2019/0240043 A1 | 8/2019 | Greenhalgh |
| 2019/0274837 A1 | 9/2019 | Eisen et al. |
| 2019/0274838 A1 | 9/2019 | Manwill et al. |
| 2019/0290447 A1 | 9/2019 | Stein |
| 2019/0314168 A1 | 10/2019 | Faulhaber |
| 2019/0321190 A1 | 10/2019 | Wagner et al. |
| 2019/0321191 A1 | 10/2019 | Glerum et al. |
| 2019/0321198 A1 | 10/2019 | Glerum et al. |
| 2019/0328540 A1 | 10/2019 | Seifert et al. |
| 2019/0336301 A1 | 11/2019 | Engstrom |
| 2019/0336302 A1 | 11/2019 | Seifert et al. |
| 2019/0358051 A1 | 11/2019 | Flower et al. |
| 2019/0374348 A1 | 12/2019 | Butler et al. |
| 2020/0008951 A1 | 1/2020 | McClintock et al. |
| 2020/0030114 A1 | 1/2020 | Cain |
| 2020/0078190 A1 | 3/2020 | Rogers et al. |
| 2020/0085586 A1 | 3/2020 | Ludwig et al. |
| 2020/0093607 A1 | 3/2020 | Davenport et al. |
| 2020/0093609 A1 | 3/2020 | Shoshtaev |
| 2020/0100904 A1 | 4/2020 | Stein et al. |
| 2020/0113706 A1 | 4/2020 | Robinson |
| 2020/0129306 A1 | 4/2020 | Miller et al. |
| 2020/0129307 A1 | 4/2020 | Hunziker et al. |
| 2021/0045891 A1* | 2/2021 | Rogers .................. A61F 2/4455 |
| 2021/0346174 A1* | 11/2021 | Flint .................. A61F 2/4611 |

FOREIGN PATENT DOCUMENTS

| | | |
|---|---|---|
| JP | 2000210315 A | 8/2000 |
| JP | 2008054710 A | 3/2008 |
| KR | 100900991 B1 | 6/2009 |
| KR | 100905962 B1 | 7/2009 |
| KR | 101235677 B1 | 2/2013 |
| RU | 2460499 C2 | 9/2012 |

\* cited by examiner

EXPANSION DRIVER

CROSS REFERENCE TO RELATED APPLICATIONS

The present patent application is a US national stage entry under 35 USC § 371 of International Patent Application No. PCT/US2022/022807, filed 31 Mar. 2022, which claims priority to U.S. Provisional Patent Application No. 63/170,345, filed Apr. 2, 2021.

BACKGROUND OF THE INVENTION

Field of the Invention

The present disclosure relates generally to medical devices, and more particularly to an instrument for use with expandable implants.

Description of the Related Art

Back problems are one of the most common and debilitating medical occurrences. In the United States alone, over 500,000 spine lumbar and cervical fusion procedures are performed each year. One of the causes of back pain and disability results from the rupture or degeneration of one or more intervertebral discs in the spine.

Surgical procedures are commonly performed to correct problems with displaced, damaged, or degenerated intervertebral discs due to trauma, disease, or aging. Generally, spinal fusion procedures involve removing some or all of the diseased or damaged disc, and inserting one or more intervertebral implants into the resulting disc space. Anterior lumbar interbody fusion (ALIF), lateral lumbar interbody fusion (XLIF), and transforaminal lumbar interbody fusion (TLIF) are techniques that spine surgeons use to access the portions of the spine to be repaired or replaced.

Replacement of injured or deteriorated spinal bone with artificial implants requires understanding and consideration of the mechanisms of the inherent stresses on the spine, as well as the biological properties of the body in response to the devices. Further, the size, configuration, and placement of an artificial implant requires precision positioning and handling by a skilled surgeon.

SUMMARY OF THE INVENTION

This disclosure includes instruments for expandable implants and methods of using the same.

In some embodiments, the instrument includes: a first driver having a first gear disposed at a first end thereof; a second driver having a second gear disposed at a first end of the second driver; and a differential operably connected to the first driver and the second driver, the differential engaging each of the first gear and the second gear. The differential is configured to transfer a torque to at least one of the first driver and the second driver.

In some embodiments, a differential for an expansion driver may include: at least one bevel gear, a first gear connected to a first output shaft, and a second gear connected to a second output shaft, the at least one bevel gear rotatably connected to a first drive source and configured to rotate around a first axis, wherein upon a rotation of the at least one bevel gear about the axis by the drive source, a torque will be transferred from the at least one bevel gear to one or more of the first gear and the second gear.

In some embodiments, a differential for an expansion driver may include: a first gear connected to a first output shaft that is configured to rotate around a first axis, a second gear connected to a second output shaft that is configured to rotate around the first axis, and a rotating carrier rotatably connected to a first drive source and configured to rotate around the first axis, wherein upon a rotation of the rotating carrier about the axis, a torque will be transferred from the rotating carrier to one or more of the first gear and the second gear.

In some embodiments, the expansion driver includes: an input shaft operably connected to at least one bevel gear, the at least one bevel gear configured to engage each of a first gear and a second gear; the first gear connected to a first output shaft; the second gear connected to a second output shaft, the second output shaft annularly disposed around at least a portion of the first output shaft; and wherein upon a rotation of the input shaft a torque is applied to at least one of the first output shaft and the second output shaft.

In some embodiments, the expansion driver includes: an input shaft operably connected to a first bevel gear and a second bevel gear, wherein the first bevel gear and the second bevel gear are configured to engage each of a first gear and a second gear; the first gear is connected to a first output shaft, the first output shaft terminating in a first driver configured to communicate with a first actuator of an expandable implant; and the second gear is connected to a second output shaft, the second output shaft annularly disposed around at least a portion of the first output shaft. At least one pinion is configured to transfer a torque from the second output shaft to a second driver extending parallel to the first driver and configured to communicate with a second actuator of the expandable implant, wherein upon a rotation of the input shaft, a torque is applied to at least one of the first driver and the second driver.

An exemplary method of treating a spinal deformity is provided, the method including: preparing an intervertebral disc space of a patient; placing an expandable implant within the prepared intervertebral disc space of the patient; and adjusting the expandable implant using an expansion driver. The expansion driver comprises: an input shaft operably connected to at least one bevel gear, the at least one bevel gear configured to engage each of a first gear and a second gear; the first gear connected to a first output shaft, the first output shaft terminating in a first driver configured to communicate with a first actuator of an expandable implant; the second gear connected to a second output shaft, the second output shaft annularly disposed around at least a portion of the first output shaft; at least one pinion configured to transfer a torque from the second output shaft to a second driver extending parallel to the first driver and configured to communicate with a second actuator of the expandable implant, wherein upon a rotation of the input shaft a torque is applied to at least one of the first driver and the second driver.

BRIEF DESCRIPTION OF THE DRAWINGS

These and other features may be further understood by those with skill in the art upon a review of the appended drawings, wherein.

DETAILED DESCRIPTION

Figure 1:
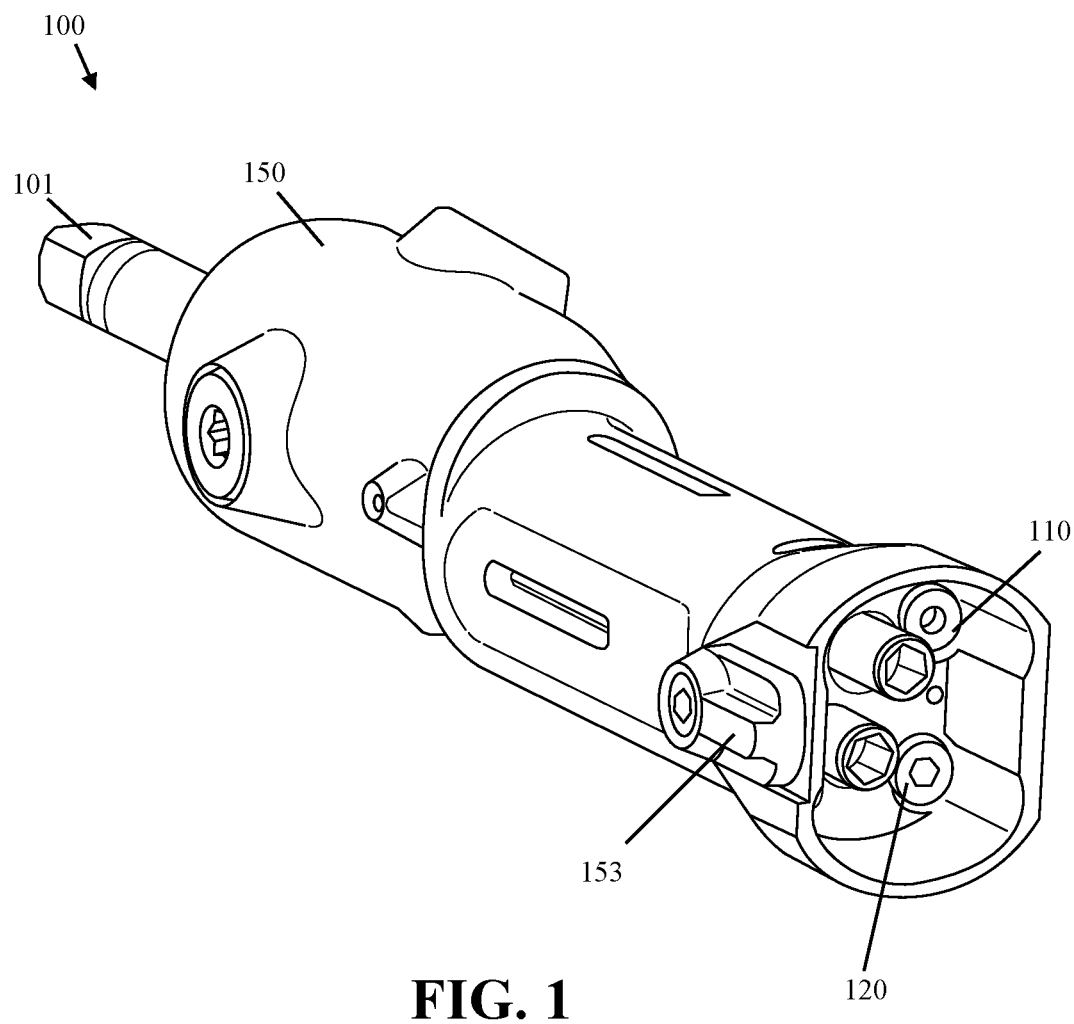
FIG. 1 shows a perspective view of an expansion driver in accordance with a first embodiment.

Illustrative embodiments are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary sill in the art having the benefit of this disclosure.

Expandable implants may include intervertebral cages, plates, distraction rods, and other adjustable medical devices. Some expandable implants may include, for example: an upper endplate, a lower endplate, and an actuator configured to change a dimension of the expandable implant. The change of dimension of the expandable implant may include a change in height, a change in width, a change in length, and a change in an angle of lordosis.

In some embodiments, an expandable implant may be designed to be inserted into the intervertebral disc space between a patient's adjacent vertebral bodies using, for example, one or more of: a lateral, posterior, and transforaminal approach. Expandable implants are generally made of any suitable biocompatible material or combination of materials. For example, the implant components may include one or more of: metal, thermoplastics such as poly ether ether ketone (PEEK), and a combination of the metal and PEEK. The expandable implant may be configured to be inserted into the disc space in a first collapsed configuration and upon being placed in a desired location within the disc space the expandable implant may be adjusted in one or more of a height, width, length, and an angle of lordosis. For example: the anterior height of the implant may be greater than the posterior height of the implant, thereby restoring a more natural lordotic curvature of a particular segment of the lumbar spine.

Adjustment of expandable implants may be accomplished for example by engaging an actuator with an expansion driver to activate the actuator and cause a movement of a first endplate relative to a second endplate to change one or more of a height, a width, a length, and an angle of lordosis of the expandable implant. The actuator may include for example at least one actuator and at least one translating wedge configured to move along the length of the at least one actuator upon a rotation of the actuator, with the wedge configured to move one or more of the first endplate and the second endplate relative to each other, to thereby change one or more of a height and an angle of lordosis of the expandable implant.

In some embodiments, the actuator of the expandable implant may include two or more actuators. In some embodiments, a first actuator is axially accessible to an expansion driver through a hollow opening in a second actuator. In other embodiments, the first actuator is disposed in an anterior portion of the implant and the hollow second actuator is disposed in an anterior portion of the implant. In some embodiments the second actuator is annularly and rotatably disposed around the first actuator. Further, in some embodiments, as disclosed below, the first actuator and the second actuator may not be coaxial. Rather, the first actuator and the second actuator may for example be parallel, and may be separated by a distance. All various placements of actuators known and used in the art of expandable interbodies are intended to be hereby contemplated and incorporated herewith.

Adjustment of expandable spinal implants may require an expansion driver. The expansion drivers described herein are capable of delivering one or more of simultaneous and equal amounts of torque to both a first actuator and a second actuator of an expandable implant that has two independent expansion mechanisms to allow for independent expansion of a first portion and a second portion of the implant.

According to an exemplary embodiment, the expansion driver has a drive source and two or more driver shafts. The input shaft and the two or more driver shafts are operably coupled by a differential for an expansion driver. A differential for an expansion driver may include at least one bevel gear, a first gear connected to a first output shaft, and a second gear connected to a second output shaft. The at least one bevel gear may be rotatably connected to a first drive source and configured to rotate around a first axis. The teeth of the at least one bevel gear may be simultaneously in communication with the teeth of the first gear and the second gear. Upon a rotation by the drive source of the at least one bevel gear, a torque may be transferred from the first drive source to the at least one bevel gear, and to one or more of the first gear and the second gear. If the first output shaft is experiencing a greater resistance from the first actuator of the implant as compared to a resistance simultaneously experienced by the second output shaft from a second actuator of the implant, the torque of the at least one bevel gear will be transferred to the second gear of the second output shaft. If the second output shaft is experiencing a greater resistance than the first output shaft, the torque of the at least one bevel gear will be transferred to the first gear of the first output shaft. If the resistance is substantially equal on the first output shaft and the second output shaft, the torque of the at least one bevel gear will be transferred to both the first gear of the first output shaft and the second gear of the second output shaft. This can be explained in that the torque effectively chooses the gear path of least resistance, and with all else being equal, drives both the first gear and the second gear.

As one with skill in the art may appreciate, a bevel gear may include a pinion and any type of known gear. Additionally, more gearing may be added to step up or step down the torque at one or more of the first drive shaft and the second drive shaft.

For example, one or more additional gears may be added between the first gear and the first output shaft to increase an amount of torque outputted at the first output shaft. Similarly, one or more additional gears may be added between the second gear and the second output shaft to increase an amount of torque outputted at the second output shaft. These gears may include planetary gear stages and similar stages known and used in the art to step up or step down torque.

Additionally, in some embodiments, the differential may include an epicyclic differential, a spur-gear differential, an active differential, a passive differential, and any other known differential.

In some embodiments, one or more pinion may be used to transfer torque from a coaxial first output shaft and second output shaft, to two parallel drivers. For example, the second output shaft may be annularly disposed around at least a portion of the first output shaft. The second output shaft may be connected to a first pinion. The first pinion may be configured to communicate a rotational motion to at least one transfer pinion, i.e., usually a first transfer pinion and a second transfer pinion. And the at least one transfer pinion may be in communication with a second pinion operably coupled to a second drive shaft. Depending on the size and number of transfer pinions used, this allows the first driver to be parallel to the second driver, despite the torque exiting the differential in a coaxial configuration.

Figure 3:
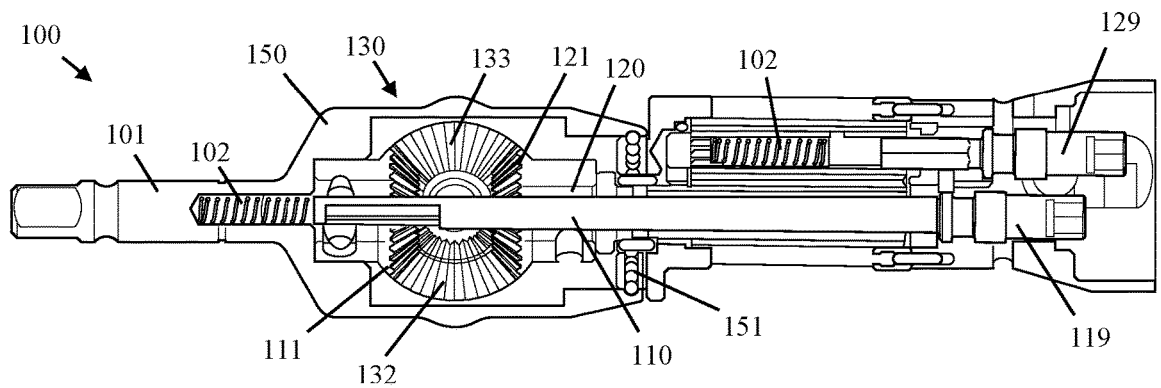
FIG. 3 shows a cross-sectional side view of the expansion driver in accordance with the first embodiment.

Turning to the drawings, FIG. 1 shows an expansion driver 100 for adjusting an expandable implant 900 (FIG. 11) including: an input shaft 101 operably connected to a differential 130 (FIG. 3). The expansion driver 100 includes a tab 153 configured to secure an expandable implant 900 to a tip of the expansion driver 100.

The internal components of the expansion driver 100 including differential 130 are shown in FIG. 3. The differential 130 includes at least one bevel gear 132, 133. The first bevel gear 132 and the second bevel gear 133 are each in communication with a first gear 111 connected to a first output shaft 110 and a second gear 121 connected to a second output shaft 120. At least a portion of the second output shaft 120 is annularly disposed around at least a portion of the first output shaft 110, and upon a rotation of the input shaft 101, a torque is configured to be applied to at least one of the first output shaft 110 and the second output shaft 120 by the differential 130.

The differential 130 in this embodiment includes a first bevel gear 132 and a second bevel gear 133, each rotatably disposed on an internal cavity of a housing 150 operably coupled to the input shaft 101. The first bevel gear 132 and the second bevel gear 133 are shown in communication with the first gear 111 connected to the first output shaft 110 and the second gear 121 connected to the second output shaft 120. Upon a rotation of the input shaft 101, the housing 150 is configured to rotate on a bearing 151 and rotate the at least one bevel gear 132, 133 around an axis of the first output shaft 110. In doing so, as will be discussed below, torque is transferred to one or more of the first output shaft 110 and the second output shaft 120 depending upon which is under the least amount of resistance at the first driver 119 and second driver 129.

A first end of the first output shaft 110 includes a first gear 111 and a second end of the first output shaft 110 includes a first driver 119. A first end of the second output shaft 120 includes a second gear 121 and a second end of the second output shaft 120 is in communication with a second driver 129. At least a portion of the second output shaft 120 is annularly disposed around at least a portion of the first output shaft 110. In this embodiment, the second driver 129 is offset from the first driver 119 and at least one pinion is included to transfer torque from the second output shaft 120 to the second driver 129 which is annularly disposed around the first output shaft 110, to the second driver 129 which extends substantially parallel to the first driver 119.

Figure 2:
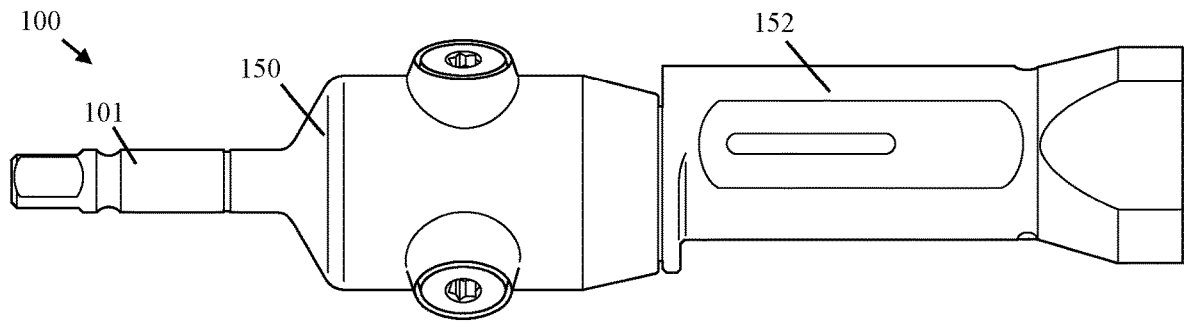
FIG. 2 shows a side view of the expansion driver in accordance with the first embodiment.
Figure 11:
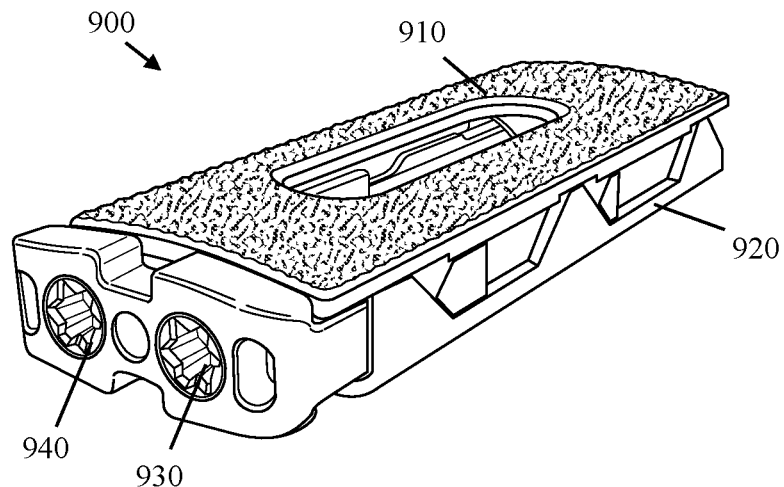
FIG. 11 shows a perspective view of an expandable implant in a first collapsed configuration.

In some embodiments, counter springs 102 are provided between the housing 150, 152 (FIG. 2) and the drivers 119, 129 (FIGS. 3-4) to keep the first driver 119 and the second driver engaged with the expandable implant 900 (FIG. 11).

Figure 4:
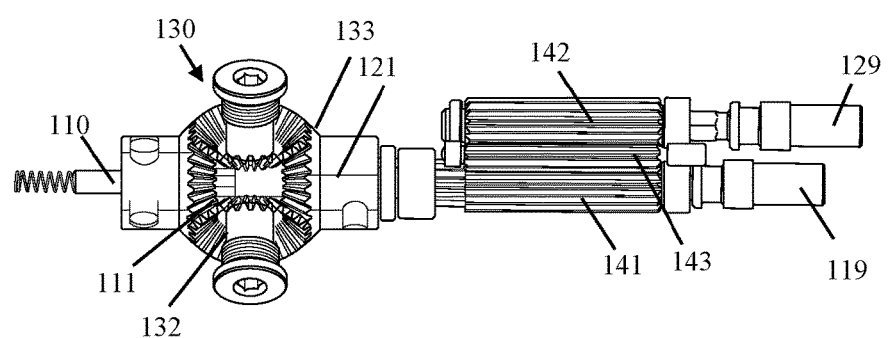
FIG. 4 shows some of the internal components of the expansion driver in accordance with the first embodiment.

FIG. 4 shows a first pinion 141 annularly disposed around at least a portion of the first output shaft 110. The teeth of the first pinion 141 are shown in communication with a first transfer pinion 143. The first transfer pinion 143 is simultaneously in communication with the second pinion 142, which is shown operably coupled to the second driver 129. The at least one pinion 141, 142, 143, 144 is configured to transfer torque from the second output 120 shaft to the second driver 129.

Figure 5:
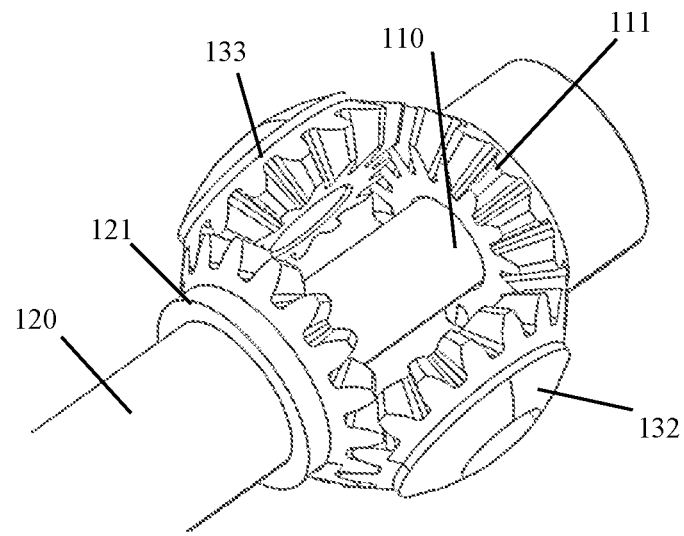
FIG. 5 shows a differential in accordance with a first embodiment including a first gear of a first driver, a second gear of a second driver, a first bevel gear and a second bevel gear.

FIG. 5 shows an enhanced view of a differential 130 in accordance with a first embodiment, including a first gear 111 of a first output shaft 110, a second gear 121 of a second output shaft 120, a first bevel gear 132, and a second bevel gear 133. The teeth of the first gear 111 are facing a direction substantially toward the teeth of the second gear 121, whereby both the first gear 111 and the second gear 121 can simultaneously communicate with each of the at least one bevel gears 132, 133. First bevel gear 132 and second bevel gear 133 are rotatably connected to a wall of a cavity connected to the input shaft 101, and are configured to rotate around an axis of the first output shaft 110 upon a rotation of the input shaft 101.

Figure 6:
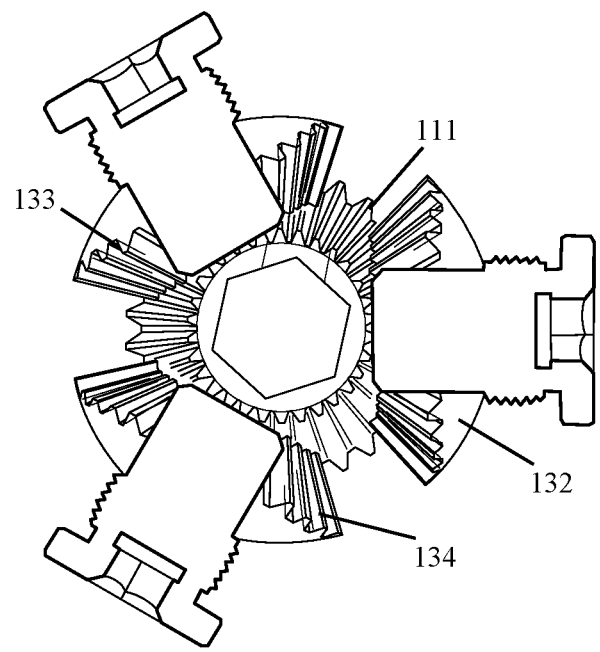
FIG. 6 shows a differential in accordance with a second embodiment including a first gear of a first driver, a second gear of a second driver, a first bevel gear, a second bevel gear, and a third bevel gear.

FIG. 6 shows an enhanced view of a differential 130 in accordance with a second embodiment including: a first gear 111 of a first output shaft 110, a second gear 121 of a second output shaft 120, a first bevel gear 132, a second bevel gear 133, and a third bevel gear 134. The teeth of the first gear 111 are again facing a direction substantially toward the teeth of the second gear 121, whereby both the first gear 111 and the second gear 121 can simultaneously communicate with each of the at least one bevel gears 132, 133, 134. Again, the first bevel gear 132, the second bevel gear 133, and the third bevel gear 134 are rotatably disposed within a cavity and operably connected to the input shaft 101, such that upon a rotation of the input shaft 101 the one or more bevel gears 132, 133, 134 are configured to rotate around an axis of the first output shaft 110.

As one with skill in the art may appreciate, a plurality of bevel gears may be added. As such, in some embodiments one, two, three, or more bevel gears may be included. Depending on the specific needs of a designer, a differential for an expansion driver may be formed by any number of bevel gears. As such only a limited number can be reasonably shown herein. Nonetheless, the use of any number of bevel gears is contemplated.

Additionally, all known and used gearing configurations for differentials are contemplated herein for use with expansion drivers.

Figure 7:
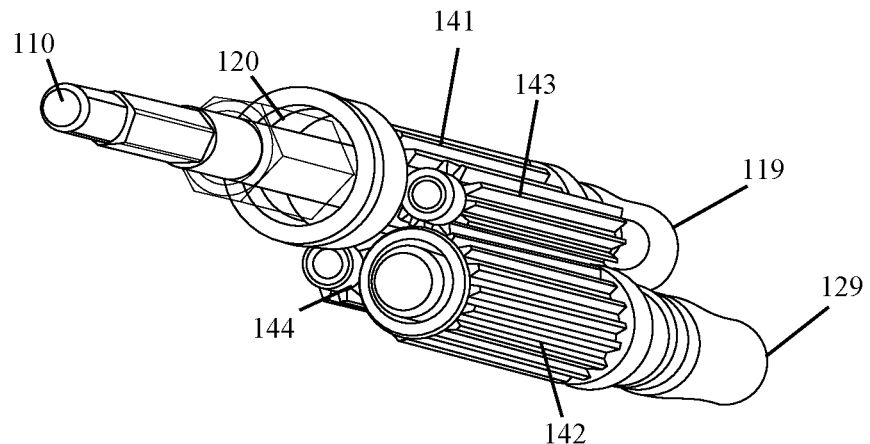
FIG. 7 shows a perspective view of a series of pinions connecting the second output shaft to the second driver.
Figure 8:
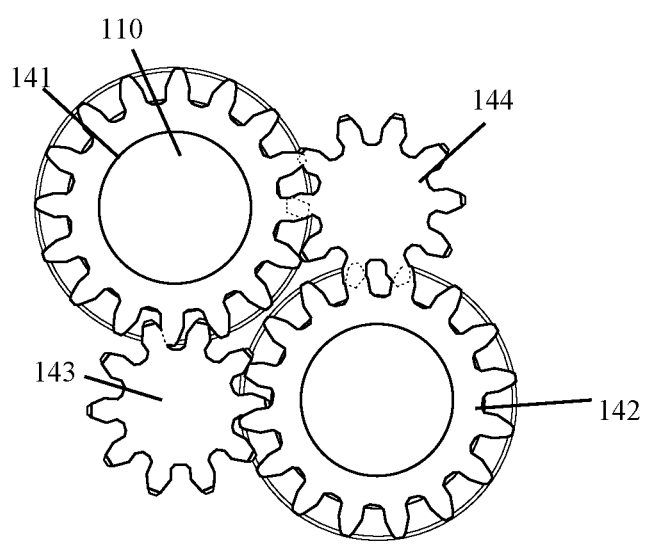
FIG. 8 shows a cross-sectional view of the series of pinions connecting the second output shaft to the second driver.

FIGS. 7 and 8 show perspective and cross sectional views of the at least one pinion 141, 142, 143, 144 configured to transfer torque from the second output shaft 120 to the second driver 129 which extends substantially parallel to the first driver 119.

FIG. 8 shows a first pinion 141 annularly disposed around at least a portion of the first output shaft 110. The teeth of the first pinion 141 are shown in communication with a first transfer pinion 143 and a second transfer pinion 144. The first transfer pinion 143 and the second transfer pinion 144 are simultaneously in communication with a second pinion 142, which is shown coupled to the second driver 129 (FIG. 7). Upon a rotation of the first pinion 141, a torque will be transferred to the first transfer pinion 143 and the second transfer pinion 144, which will in turn rotate the second pinion 142 and ultimately the second driver 129.

Figure 9:
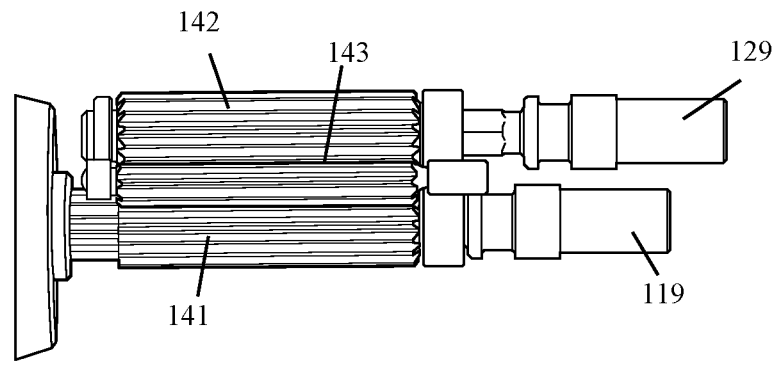
FIG. 9 shows an enhanced view of the tip of the expansion driver including the first driver and the second driver.
Figure 10:
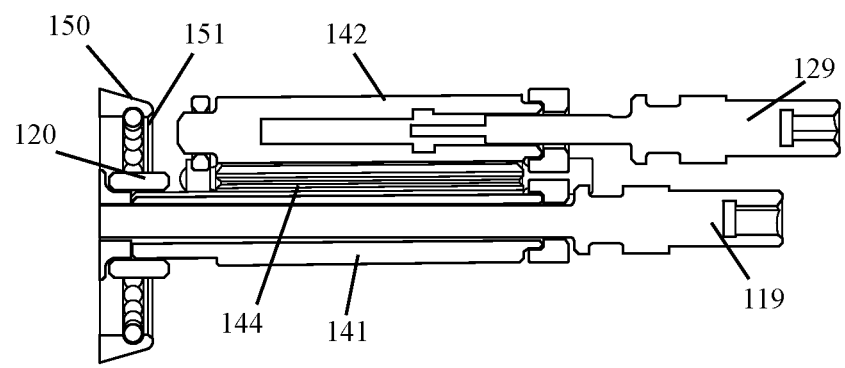
FIG. 10 shows a cross-sectional view of the tip of the expansion driver including the first driver and the second driver.

FIG. 9 shows the tip of the expansion driver 100 including a first driver 119 and a second driver 129. The first driver 119 is configured to communicate with a first actuator 930 of an expandable implant 900 (FIG. 11). The second driver 129 is configured to communicate with a second actuator 940 of an expandable implant 900.

FIG. 11 shows an expandable implant 900 in a first collapsed configuration. The expandable implant 900 includes: a first endplate 910, a second endplate 920, a first actuator 930 and a second actuator 940, wherein upon a rotation of one or more of the first actuator 930 and the second actuator 940, the first endplate 910 and the second endplate 920 are configured to move and to thereby change a dimension of the expandable implant 900.

As discussed above, the expansion driver 100 is configured to adjust the expandable implant 900 within the intervertebral disc space of a patient. In some embodiments, the expandable implant 900 may be removably secured to a tip of the expansion driver to place and adjust the expandable implant within the intervertebral disc space of a patient. The first driver 119 will be in communication with the first actuator 930 of the expandable implant 900, and configured to adjust the expandable implant 900 upon a rotation of the first driver 119. The second driver 129 will be in communication with the second actuator 940 of the expandable implant 900, and configured to adjust the expandable implant 900 upon a rotation of the second driver 129.

Figure 12:
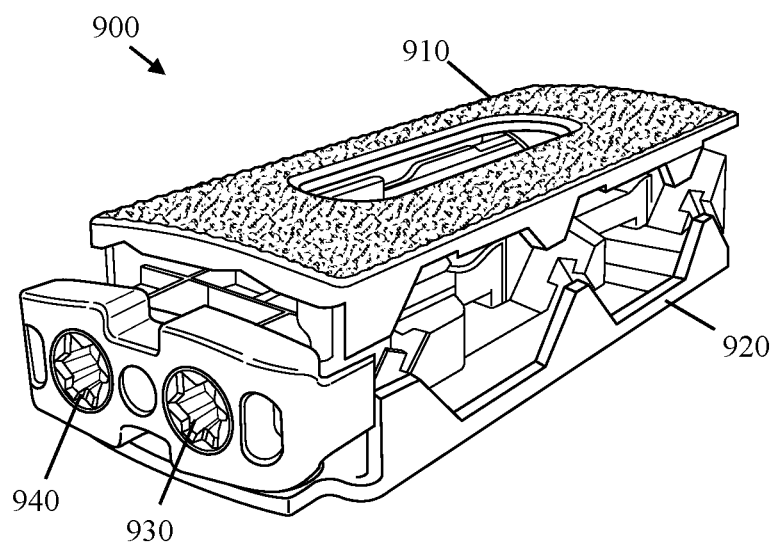
FIG. 12 shows a perspective view of the expandable implant in a second expanded configuration.

FIG. 12 shows a rear perspective view of the expandable implant 900 expanded into a second configuration. When the first actuator 930 and the second actuator 940 are rotated such that a first translating member and a second translating member move a substantially equal amount, this movement will expand the expandable implant 900, thereby changing the height of the expandable implant 900.

Figure 13:
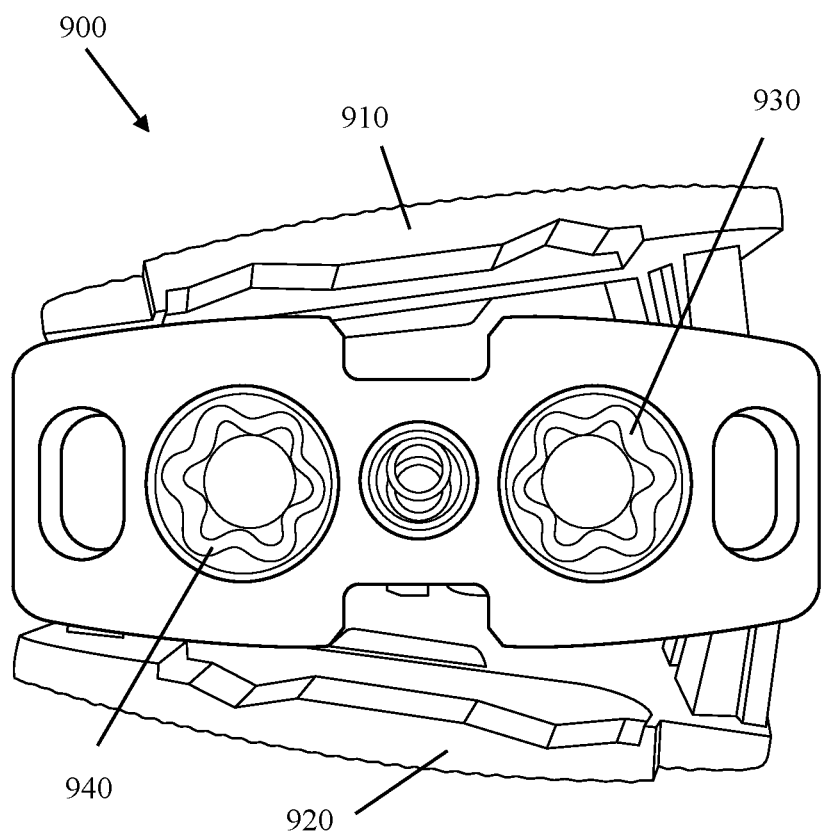
FIG. 13 shows a rear view of the expandable implant in a third expanded configuration.

FIG. 13 shows a rear perspective view of the expandable implant 900 expanded into a third configuration. When the first actuator 930 and the second actuator 940 are rotated such that a first translating member and a second translating member do not move a substantially equal amount, this movement will change an angle of lordosis of the expandable implant 900, thereby changing the height of the expandable implant 900.

Now, expandable implants 900 placed between vertebral bodies of a patient experience numerous forces, particularly during adjustment. As one with skill in the art may appreciate, in an expandable implant 900 having an actuator including a first actuator 930 and a second actuator 940, each actuator is going to experience a different amount of resistance upon adjustment which depends on an instantaneous load and state of the vertebral bodies relative to the expandable implant 900. When driving the first actuator 930 and the second actuator 940 using a fixed expansion driver, for example, unequal resistance can result in uneven and often undesired adjustment of the expandable implant 900. In the instant embodiment however, the differential 130 allows for selective driving by the expansion driver 100 to deliver a desired amount of torque.

For example, when a first amount of resistance from the first actuator 930 on the first driver 119 is less than a second amount of resistance from the second actuator 940 on the second driver 129, the first bevel gear 132 and the second bevel gear 133 of the differential 130 are configured to rotate the first driver 119 upon a rotation of the input shaft 101. The first driver 119 will in turn rotate the first actuator 930 to thereby adjust the expandable implant 900. The second driver 129 will not adjust the second actuator 940, and thus the first actuator 930 will continue to be rotated adjusting the angle of lordosis of the expandable implant 900 until a substantially equal amount of resistance is observed by the first actuator 930 and the second actuator 940.

When a first amount of resistance from the first actuator 930 on the first driver 119 is greater than a second amount of resistance of the second actuator 940 on the second driver 129, the first bevel gear 132 and the second bevel gear 133 are configured to rotate the second driver 129. The second driver 129 will in turn rotate the second actuator 940 to thereby adjust the expandable implant 900. The first driver 119 will not adjust the first actuator 930, and thus the second actuator 940 will continue to be rotated, adjusting the angle of lordosis of the expandable implant 900 until a substantially equal amount of resistance is observed by the first actuator 930 and the second actuator 940.

When a first amount of resistance from the first actuator 930 on the first driver 119 is substantially equal to a second amount of resistance of the second actuator 940 on the second driver 129, the first bevel gear 132 and the second bevel gear 133 are configured to rotate both the first driver 119 and the second driver 129. The first driver 110 will in turn rotate the first actuator 930, the second driver 120 will in turn rotate the second actuator 940, and both actuators will simultaneously adjust the expandable implant 900. As one with skill in the art may appreciate, in the instant embodiment of an expandable implant 900 simultaneous adjustment of the first actuator 930 and the second actuator 940 will result in a change in height of the expandable implant 900.

The expansion driver 100 is configured such that upon activation of a drive source which may include a rotation of a handle operably coupled to the input shaft 101, a torque is transferred from the input shaft 101 to the first bevel gear 132 and the second bevel gear 133, with the first bevel gear 132 and the second bevel gear 133 configured to rotate one or more of the first output shaft 110 and the second output shaft 120, depending on an amount of resistance experienced at the expandable implant 900. Further the first output shaft 110 terminates in the first driver 119, and the second output shaft extends annularly along at least a portion of the first output shaft 110 and is connected to a first pinion 141. The first pinion is in communication with at least one transfer pinion 143, 144 and the at least one transfer pinion 143, 144 is in communication with a second pinion 142, which is connected to a second driver 129. Therefore, rotation of the first output shaft 110 results in rotation of the first driver 119, and rotation of the second output shaft 120 results in rotation of the second driver 129.

Some or all of the foregoing components may be fabricated using known machining and additive manufacturing techniques. The drivers may be fabricated from known biocompatible materials including aluminum, steel, and titanium. Additionally, the handle may be fabricated from materials including: a polymeric material, carbon fiber, and metals.

According to one exemplary method of adjusting an expandable implant, the steps may include: preparing an intervertebral disc space of a patient; placing an expandable implant within the prepared intervertebral disc space of the patient; and adjusting the expandable implant using an expansion driver as described herein. In particular, the expansion driver used in the present method may comprise: an input shaft operably connected to at least one bevel gear, the at least one bevel gear configured to engage each of a first gear and a second gear; the first gear connected to a first output shaft, the first output shaft terminating in a first driver configured to communicate with a first actuator of an expandable implant; the second gear connected to a second output shaft, the second output shaft annularly disposed around at least a portion of the first output shaft; and at least one pinion configured to transfer a torque from the second output shaft to a second driver extending parallel to the first driver and configured to communicate with a second actuator of the expandable implant. The adjusting may further comprise rotating the input shaft, which in turn applies a torque to at least one of the first driver and the second driver.

To prepare the intervertebral disc space of the patient, the surgeon may first gain access to the intervertebral disc space via one or more of for example: an anterior, a lateral, a transforaminal and a posterior approach. The intervertebral disc may be partially or totally removed from the disc space. The contact surfaces of the adjacent vertebral bodies may be prepared to help promote fusion.

The expandable implant may be provided to the disc space by an insertion device, for example one or more of: an inserter and the expansion driver. First the expandable implant may be removably secured to the insertion device. Next the expandable implant may be placed within the prepared intervertebral disc space using, for example, a posterior, transforaminal or lateral approach. If an inserter is used, the inserter may be removed and an expansion driver may then be secured to the implant and used to adjust the expandable implant. If the expansion driver is used to insert the expandable implant, the next step is simply achieving a desired adjustment.

As described above, the expandable implant may be designed to be adjusted in one or more of a height, a length, a width and an angle of lordosis of the expandable implant. The expandable implant may be dimensioned according to the size of the patient. The handle of the expansion driver would be rotated, to adjust the expandable implant to the desired height, length, width, and angle of lordosis. Once the surgeon or user is satisfied with the amount of adjustment, the expansion driver may be removed from the expandable implant, and subsequently the patient, whilst leaving the expandable implant adjusted within the intervertebral space of the patient.

It may be desirable for the surgeon to pack one or more of the expandable implant and the intervertebral disc space using a bone graft or bone graft substitute material to promote fusion. Fixation plates may be applied to one or more of the vertebral bodies and the expandable implant to secure the expandable implant within the intervertebral disc space. Finally, all placement and expansion instrumentation may be removed and the access hole closed, to allow for the fusion and healing processes to begin.

Figure 14:
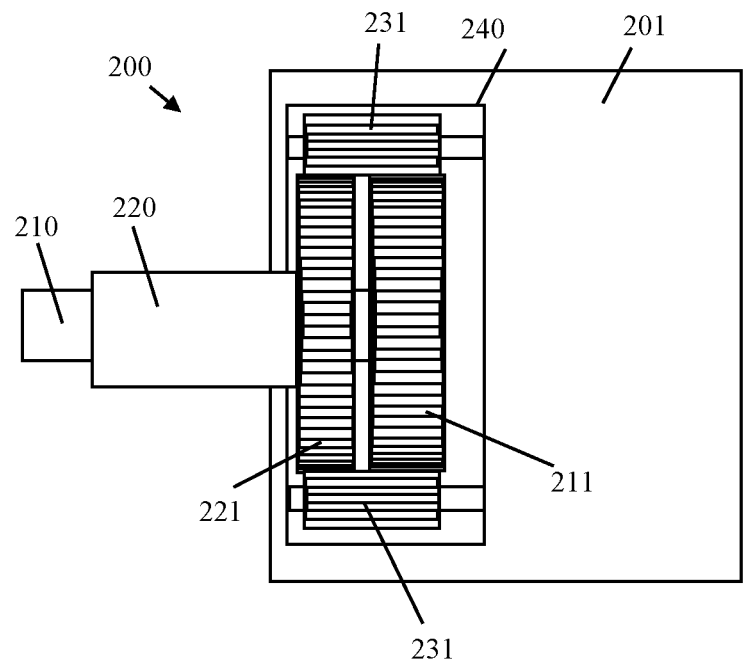
FIG. 14 shows a side view of an expansion driver having a differential in accordance with a third embodiment.

FIG. 14 shows a schematic of a differential 230 for an expansion driver 200 in accordance with a second embodiment according to the invention. Expansion driver 200 may include: a first gear 211 disposed at the first end of a first output shaft 210, a second gear 221 disposed at the first end of a second output shaft 220, and a rotating carrier 230 having one or more pinions 231. Upon a rotation of the rotating carrier 230, a torque is applied to one or more of the first output shaft 210 and the second shaft 220.

Figure 15:
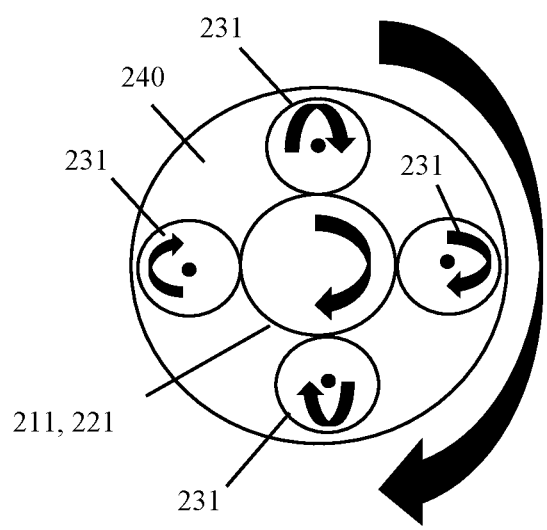
FIG. 15 shows a schematic top view of a rotating carrier of the expansion driver in accordance with the third embodiment of FIG. 14.

As previously described, the differential 230 includes a rotating carrier 230 having at least one pinion 231. In this embodiment there are four individual pinions 231, each configured to communicate with the first gear 211 and the second gear 221. Upon a rotation of the rotating carrier 230, which may be caused by rotation of the handle 201, as indicated in FIG. 15, the four pinions 231 are configured to rotate around the axis of the first output shaft 210, and thereby rotate at least one of the first gear 211 and the second gear 221, depending on which is experiencing less input resistance, as discussed above. It is contemplated that this design for a differential could be used in the aforementioned embodiments.

Exemplary embodiments herein have been directed to expandable implants configured for adjustment in height and angle of lordosis. It is contemplated that devices within the scope of this disclosure could be used to adjust expandable implants which are adjustable in height, length, width, angle of lordosis, and any change of dimension. The chosen embodiments should not be construed as limiting and this disclosure is intended to encompass the due bounds as presented in the claims.

What is claimed is:

1. An expansion driver for adjusting an expandable implant, comprising:
    an input shaft operably connected to at least one bevel gear,
    the at least one bevel gear configured to engage each of a first gear and a second gear;
    the first gear connected to a first output shaft,
    the first output shaft terminating in a first driver configured to communicate with a first actuator of an expandable implant;
    the second gear connected to a second output shaft,
    the second output shaft annularly disposed around at least a portion of the first output shaft;
    and
    a housing operatively coupled to the input shaft,
    wherein the first output shaft and the second output shaft extend through the housing; and
    wherein upon a rotation of the input shaft, the housing is configured to rotate which rotates the at least one bevel gear so that a torque is applied to at least one of the first output shaft and the second output shaft.

2. The expansion driver of claim 1, wherein the at least one bevel gear comprises a first bevel gear and a second bevel gear, the first bevel gear and the second bevel gear being configured to engage each of the first gear and the second gear.

3. The expansion driver of claim 2, wherein the first driver is configured to rotate the first actuator of the expandable implant to adjust an angle of the expandable implant.

4. The expansion driver of claim 3, further comprising at least one pinion configured to transfer a torque from the second output shaft to a second driver configured to communicate with a second actuator of the expandable implant.

5. The expansion driver of claim 4, wherein the second driver is offset from and extends in a direction substantially parallel to the first driver.

6. The expansion driver of claim 5, further comprising a handle configured to rotate the input shaft upon a rotation of the handle.

7. The expansion driver of claim 6, wherein the handle is configured to transfer a torque to the input shaft, and the input shaft is configured to rotate the first bevel gear and the second bevel gear.

8. The expansion driver of claim 7, wherein upon the rotation of the first bevel gear and the second bevel gear, a torque is applied to at least one of the first driver and the second driver.

9. The expansion driver of claim 8, wherein when a first amount of resistance on the first driver is less than a second amount of resistance on the second driver, the first bevel gear and the second bevel gear are configured to rotate the first driver.

10. The expansion driver of claim 8, wherein when a first amount of resistance on the first driver is more than a second amount of resistance on the second driver, the first bevel gear and the second bevel gear are configured to rotate the second driver.

11. The expansion driver of claim 8, wherein when a first amount of resistance on the first driver is equal to a second amount of resistance on the second driver, the first bevel gear and the second bevel gear are configured to rotate both the first driver and the second driver.

12. An expansion driver configured to adjust an expandable implant, comprising:
an input shaft operably connected to a first bevel gear and a second bevel gear,
the first bevel gear and the second bevel gear configured to engage each of a first gear and a second gear;
the first gear connected to a first output shaft,
the first output shaft terminating in a first driver configured to communicate with a first actuator of an expandable implant;
the second gear connected to a second output shaft,
the second output shaft annularly disposed around at least a portion of the first output shaft;
at least one pinion configured to transfer a torque from the second output shaft to a second driver extending parallel to the first driver and configured to communicate with a second actuator of the expandable implant;
and
a housing operatively coupled to the input shaft,
wherein the first output shaft and the second output shaft extend through the housing; and
wherein upon a rotation of the input shaft, the housing is configured to rotate which rotates the first and second bevel gears so that a torque is applied to at least one of the first driver and the second driver.

13. The expansion driver of claim 12, further comprising a handle configured to rotate the input shaft upon a rotation of the handle.

14. The expansion driver of claim 13, wherein the handle is configured such that upon the rotation of the handle the torque is transferred from the handle to the input shaft, and the input shaft is configured to rotate the first bevel gear and the second bevel gear.

15. The expansion driver of claim 14, wherein upon the rotation of the first bevel gear and the second bevel gear, a torque is applied to at least one of the first driver and the second driver.

16. The expansion driver of claim 14, wherein when a first amount of resistance on the first driver is less than a second amount of resistance on the second driver, the first bevel gear and the second bevel gear are configured to rotate the first driver.

17. The expansion driver of claim 14, wherein when a first amount of resistance on the first driver is more than a second amount of resistance on the second driver, the first bevel gear and the second bevel gear are configured to rotate the second driver.

18. The expansion driver of claim 14, wherein when a first amount of resistance on the first driver is equal to a second amount of resistance on the second driver, the first bevel gear and the second bevel gear are configured to rotate both the first driver and the second driver.

* * * * *